(12) United States Patent
Schäfer et al.

(10) Patent No.: US 9,295,978 B2
(45) Date of Patent: Mar. 29, 2016

(54) CATALYST AND METHOD FOR THE DIRECT SYNTHESIS OF DIMETHYL ETHER FROM SYNTHESIS GAS

(71) Applicant: BASF Corporation, Florham Park, NJ (US)

(72) Inventors: Alexander Schäfer, Limburgerhof (DE); Rostam Jal Madon, Flemington, NJ (US); Thorsten von Fehren, Bürstadt (DE)

(73) Assignee: BASF Corporation, Florham Park, NJ (US)

( * ) Notice: Subject to any disclaimer, the term of this patent is extended or adjusted under 35 U.S.C. 154(b) by 368 days.

(21) Appl. No.: 13/767,276

(22) Filed: Feb. 14, 2013

(65) Prior Publication Data

US 2013/0211148 A1  Aug. 15, 2013

Related U.S. Application Data

(60) Provisional application No. 61/599,116, filed on Feb. 15, 2012.

(51) Int. Cl.
| | |
|---|---|
| *B01J 23/00* | (2006.01) |
| *B01J 21/02* | (2006.01) |
| *B01J 27/14* | (2006.01) |
| *B01J 23/02* | (2006.01) |
| *B01J 27/18* | (2006.01) |
| *B01J 23/80* | (2006.01) |
| *C07C 41/09* | (2006.01) |
| *C07C 41/01* | (2006.01) |
| *B01J 37/03* | (2006.01) |
| *B01J 37/04* | (2006.01) |
| *B01J 37/06* | (2006.01) |
| *B01J 23/20* | (2006.01) |
| *B01J 23/83* | (2006.01) |
| *B01J 23/847* | (2006.01) |
| *B01J 35/00* | (2006.01) |
| *B01J 21/04* | (2006.01) |
| *B01J 27/185* | (2006.01) |
| *B01J 35/02* | (2006.01) |
| *B01J 37/00* | (2006.01) |

(52) U.S. Cl.
CPC .............. *B01J 27/1817* (2013.01); *B01J 23/20* (2013.01); *B01J 23/80* (2013.01); *B01J 23/83* (2013.01); *B01J 37/031* (2013.01); *B01J 37/04* (2013.01); *B01J 37/06* (2013.01); *C07C 41/01* (2013.01); *C07C 41/09* (2013.01); *B01J 21/04* (2013.01); *B01J 23/8474* (2013.01); *B01J 23/8476* (2013.01); *B01J 27/14* (2013.01); *B01J 27/1853* (2013.01); *B01J 35/0006* (2013.01); *B01J 35/023* (2013.01); *B01J 37/0009* (2013.01); *B01J 2523/00* (2013.01)

(58) Field of Classification Search
CPC ................... B01J 2523/48; B01J 2523/3712; B01J 2323/31; B01J 2523/27; B01J 2523/17; B01J 27/14; B01J 23/8476; B01J 23/8474; C07C 41/01
USPC .................................. 502/202, 208, 304, 342
See application file for complete search history.

(56) References Cited

U.S. PATENT DOCUMENTS

| | | |
|---|---|---|
| 3,850,850 A | 11/1974 | Collins |
| 3,923,694 A | 12/1975 | Cornthwaite |
| 4,111,847 A | 9/1978 | Stiles |
| 4,535,071 A | 8/1985 | Schneider et al. |
| 4,598,061 A | 7/1986 | Schneider et al. |
| 4,666,945 A | 5/1987 | Osugi et al. |
| 4,788,175 A | 11/1988 | Short et al. |
| 4,863,894 A | 9/1989 | Chinchen et al. |
| 5,302,569 A | 4/1994 | Horn et al. |
| 5,569,792 A | 10/1996 | Deckers et al. |
| 6,103,005 A | 8/2000 | Sare et al. |
| 6,346,145 B1 | 2/2002 | Hen et al. |
| 7,091,155 B2 | 8/2006 | Inui et al. |
| 7,601,662 B2 | 10/2009 | Bull et al. |
| 8,016,936 B2 | 9/2011 | Yildirim et al. |
| 8,669,295 B2 * | 3/2014 | Fu et al. .................. 518/714 |
| 2002/0088376 A1 | 7/2002 | Sare et al. |
| 2004/0127587 A1 | 7/2004 | Espinoza et al. |
| 2004/0132834 A1 | 7/2004 | Ortego et al. |
| 2005/0080148 A1 | 4/2005 | Ladebeck et al. |
| 2005/0234137 A1 | 10/2005 | Espinoza et al. |
| 2006/0118664 A1 | 6/2006 | Sare et al. |

(Continued)

FOREIGN PATENT DOCUMENTS

| | | |
|---|---|---|
| CA | 1159435 | 12/1983 |
| CN | 92100590.3 | 1/1992 |

(Continued)

OTHER PUBLICATIONS

International Search Report Jun. 21, 2013.

(Continued)

*Primary Examiner* — Jafar Parsa

(74) *Attorney, Agent, or Firm* — Lowenstein Sandler LLP

(57) ABSTRACT

Catalysts and methods for their manufacture and use for the synthesis of dimethyl ether from syngas are disclosed. The catalysts comprise ZnO, CuO, $ZrO_2$, alumina and one or more of boron oxide, tantalum oxide, phosphorus oxide and niobium oxide. The catalysts may also comprise ceria. The catalysts described herein are able to synthesize dimethyl ether directly from synthesis gas, including synthesis gas that is rich in carbon monoxide.

15 Claims, No Drawings

(56) References Cited

U.S. PATENT DOCUMENTS

| | | |
|---|---|---|
| 2008/0125311 A1 | 5/2008 | Baek et al. |
| 2009/0048355 A1 | 2/2009 | Polier et al. |
| 2009/0149324 A1 | 6/2009 | Madon et al. |
| 2009/0312581 A1 | 12/2009 | Urtel et al. |
| 2009/0312588 A1 | 12/2009 | Hatscher et al. |
| 2009/0325794 A1 | 12/2009 | Wolk et al. |
| 2010/0102278 A1 | 4/2010 | Madon et al. |
| 2010/0160694 A1 | 6/2010 | Fitzpatrick et al. |
| 2011/0118367 A1 | 5/2011 | Kamg et al. |
| 2011/0172085 A1 | 7/2011 | Wolk et al. |

FOREIGN PATENT DOCUMENTS

| | | |
|---|---|---|
| CN | 1883804 | 12/2006 |
| CN | 101121143 | 2/2008 |
| CN | 101722002 | 6/2010 |
| EP | 0721799 | 7/1996 |
| EP | 0794006 | 9/1997 |
| EP | 1011856 | 4/2003 |
| GB | 2202531 | 9/1988 |
| JP | 60084142 | 5/1985 |
| JP | 6254414 | 9/1994 |
| JP | 6320000 | 11/1994 |
| JP | 7024320 | 1/1995 |
| JP | 7039755 | 2/1995 |
| JP | 7039756 | 2/1995 |
| JP | 8215576 | 8/1996 |
| JP | 10272360 | 10/1998 |
| JP | 2001/205089 | 7/2001 |
| JP | 2010/069453 | 4/2010 |
| KR | 100812100 | 3/2008 |
| WO | WO-03/053575 | 7/2003 |
| WO | WO-2006/117190 | 11/2006 |
| WO | WO-2007/110176 | 10/2007 |
| WO | WO-2009/076119 | 6/2009 |
| WO | WO-2010/146379 | 12/2010 |
| WO | WO-2010/146380 | 12/2010 |
| WO | WO-2011/016759 | 2/2011 |

OTHER PUBLICATIONS

Machine Translation of CN-101121143, 6 pages.

* cited by examiner

CATALYST AND METHOD FOR THE DIRECT SYNTHESIS OF DIMETHYL ETHER FROM SYNTHESIS GAS

CROSS-REFERENCE TO RELATED APPLICATIONS

This application claims priority to U.S. Provisional Application No. 61/599,116, filed Feb. 15, 2012, the entire contents of which are hereby incorporated by reference.

TECHNICAL FIELD

The invention relates to catalysts, methods for preparing catalysts and methods using the catalyst to produce dimethyl ether from synthesis gas.

BACKGROUND

Fossil fuels are known to have the disadvantages of being a finite resource and a cause of global warming. As such, there has been much research on alternative fuels due to these ecological and economical considerations. Among the alternative fuels, dimethyl ether (DME) is a clean fuel, and can be synthesized from synthesis gas, also known as syngas. Synthesis gas is a mixture of mainly hydrogen, carbon monoxide and carbon dioxide that can be generated from a variety of different primary sources. These primary sources can include natural gas, coal, heavy oil, and also from biomass. The syngas is passed over a catalyst to produce methanol according to the following chemical equation:

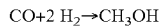

$$CO + 2H_2 \rightarrow CH_3OH$$

Methanol can then be converted into DME by dehydration over an acidic catalyst according to the following chemical equation:

$$2 CH_3OH \rightarrow CH_3OCH_3 + H_2O$$

In the direct DME production there are mainly two overall reactions that occur from synthesis gas. These reactions, reaction (1) and reaction (2), are listed below.

$$3 CO + 3H_2 \rightarrow CH_3OCH_3 + CO_2 \quad (1)$$

$$2 CO + 4H_2 \rightarrow CH_3OCH_3 + H_2O \quad (2)$$

Reaction (1) is a combination of three reactions, which are methanol synthesis reaction, methanol dehydration reaction, and water gas shift reaction:

$$2 CO + 4H_2 \rightarrow 2 CH_3OH \quad \text{(methanol synthesis reaction)}$$

$$2CH_3OH \rightarrow CH_3OCH_3 + H_2O \quad \text{(methanol dehydration reaction)}$$

$$CO + H_2O \rightarrow CO_2 + H_2 \quad \text{(water gas shift reaction)}$$

The reaction (1) has a stoichiometric ratio $H_2/CO$ of 1:1 and has some advantages over reaction (2). For example reaction (1) generally allows higher single pass conversions and less energy-consuming in comparison to the removal of water from the system in reaction (2).

Recently, attention has been directed towards the direct synthesis of dimethyl ether from synthesis gas using a catalytic system that combines a methanol synthesis catalyst and a catalyst for dehydration of said alcohol. Depending on the synthesis gas used, the catalyst might additionally show water gas shift activity. However, the processes for the preparation of dimethyl ether according to the prior art have the drawbacks that additional steps have to be taken to get an efficient DME production. Additionally, the catalyst used in the methods known in the prior art do not achieve the thermodynamic possibilities. Therefore it is still desirable to increase the yield of DME in the synthesis gas conversion, and do so in one step.

SUMMARY

A first aspect of the invention relates to a catalyst composition for the synthesis of dimethyl ether. The catalyst composition comprises about 10 to about 75 weight % CuO; about 5 to about 50 weight % ZnO; about 1 to about 30 weight % $ZrO_2$; about 1 to about 40 weight % of one or more of boron oxide, niobium oxide, tantalum oxide, phosphorus oxide, and combinations thereof; and about 5 to about 80 weight % alumina, wherein at least a portion of alumina comprises γ-alumina. In one or more embodiments, the catalyst composition further comprises ceria. In some embodiments, the catalyst composition comprises about 1 to about 30 weight % of ceria.

In one or more embodiments, the catalyst comprises about 0.1 to about 20 weight % of one or more of boron oxide, tantalum oxide, phosphorus oxide, niobium oxide and combinations thereof. In some embodiments, the alumina comprises one or more of dispersible alumina, γ-alumina, η-alumina, χ-alumina, other transitional aluminas, boehmite, pseudoboehmite, gibbsite, bayerite, and mixtures thereof. In one or more embodiments, the alumina consists essentially of γ-alumina. In some embodiments, the alumina consists essentially of dispersible alumina and γ-alumina.

In one or more embodiments, the alumina comprises dispersible alumina that has a dispersibility of at least about 70% or greater. In some embodiments, at least a portion of the dispersible alumina is replaced with a γ-alumina. In one or more embodiments, at least a portion of the dispersible alumina is replaced with a γ-alumina. In some embodiments, the catalyst composition comprises boron oxide, and the alumina comprises gamma alumina. In one or more embodiments, the catalyst composition comprises niobium oxide, and the alumina comprises gamma alumina.

In some embodiments, at least a portion of the alumina comprises alumina prepared by peptizing dispersible alumina with a dispersibility of at least about 50% or greater and reacting the alumina with precursors of CuO, ZnO, and $ZrO_2$. In one or more embodiments, a portion of the alumina comprises alumina prepared by peptizing dispersible alumina with a dispersibility of at least about 50% or greater. In some embodiments, the alumina comprises γ-alumina. In one or more embodiments, the alumina consists essentially of γ-alumina. In one or more embodiments, the catalyst composition has a high copper dispersion.

Another aspect of the invention pertains to a method of making dimethyl ether. The method comprises contacting a stream of synthesis gas comprising carbon monoxide and hydrogen with any variations of the catalyst described above. In one or more embodiments, the synthesis gas has a ratio of carbon monoxide to hydrogen is about 1. In some embodiments, the synthesis gas has a ratio of carbon monoxide to hydrogen is less than about 1. In one or more embodiments, the synthesis gas has a ratio of carbon monoxide to hydrogen is greater than about 1. In some embodiments, the synthesis gas further comprises carbon dioxide.

Yet another aspect of the invention relates to methods of producing one or more of the described catalyst compositions. In one or more embodiments, the method comprises preparing a first powder, preparation of the first powder comprising (i) forming a first slurry by peptizing a dispersible alumina in an acid at a pH between 2 and 5 and a temperature of about 20° C. to 30° C.; (ii) forming a second slurry of zirconyl nitrate and water at a pH of less than about 1.5 and a temperature in the range of about 20° C. to 30° C.; and (iii) calcining the first and second slurries to provide a first powder; preparing a second powder, preparation of the second powder comprising calcinng a salt comprising niobium, tantalum, phosphorus or boron with a mixture of γ-alumina; and mixing the first and second powder. In one or more embodiments, the ratio of the first powder makes up about 70 to about 90% by weight of the total catalyst.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

As used herein, the term "synthesis gas" is used synonymously with "syngas," and refers to a gas mixture comprising carbon monoxide (CO) and hydrogen ($H_2$). The gas may also comprise carbon dioxide ($CO_2$). The relative amounts of the various components may differ.

As used herein, the term "calcination" refers to a thermal treatment process applied to ores and other solid materials to bring about a thermal decomposition, phase transition, or removal of a volatile fraction. The calcination process normally takes place at temperatures below the melting point of the product materials, and is done under an oxygen-containing atmosphere. In some cases, the calcination can be performed under an inert atmosphere (e.g. nitrogen).

A first aspect of the present invention pertains to a dimethyl ether catalyst comprising CuO, ZnO, $ZrO_2$, $Al_2O_3$ and one or more of niobium oxide, tantalum oxide, boron oxide, phosphorus oxide and combinations thereof. In a particular embodiment, the amount of CuO has a range of about 10 to about 75 weight percent of the catalyst. In an even more particular embodiment, the catalyst composition has a high copper dispersion. In another embodiment, the amount of ZnO has a range of about 5 to about 50 weight percent. In other embodiments, the catalyst composition comprises from about 1 to about 30 weight percent $ZrO_2$. In yet another embodiment, the about of alumina ranges from about 5 to about 80 weight percent alumina. In some embodiments, the amount of boron oxide, tantalum oxide, niobium oxide, phosphorus oxide or combinations thereof, has a range of about 0.1 to about 40 weight percent. In other specific embodiments, the amount of boron oxide, tantalum oxide, niobium oxide, phosphorus oxide or combinations thereof, has arrange of about 0.1 to about 20 weight percent. In one or more embodiments, the catalyst composition further comprises ceria. In a more specific embodiment, the catalyst composition comprises about 1 to about 30% of ceria.

As used herein, percents given in terms of weight are relative to the weight of the final catalyst composition, unless otherwise stated.

The catalyst composite comprises alumina, which can come in various forms. For example, one or more embodiments may comprise one or more of dispersible alumina, γ-alumina, η-alumina, χ-alumina, other transitional aluminas, boehmite, pseudoboehmite, gibbsite, bayerite, and mixtures thereof.

In certain embodiments where the alumina comprises dispersible alumina, it has a dispersibility of at least about 70% or greater. As used herein, the term "dispersible alumina" refers to the amount of alumina that becomes colloidal at a certain pH, which is typically in the acid range, a process that is referred to as acid peptizing. Acid peptizing results in the formation of particles that are less than 1 micron (μm). Examples of dispersible alumina include alumina having 40% or greater dispersibility in water after peptizing at a pH of 2 to 5. Other examples of alumina having 50% or greater dispersibility, 60% or greater dispersibility, 70% or greater dispersibility, 80% or greater dispersibility, or 90% or greater dispersibility in water after peptizing at a pH of 2 to 5 are included in this definition of dispersible alumina. As used herein, the percent dispersibility of alumina refers to the percentage of alumina that is less than 1 micron in size in the acidic solution after peptizing at a pH from about 2 to about 5. Non-limiting examples of aluminas that are dispersible include boehmite or pseudo-boehmite aluminas. In some embodiments, the alumina utilized in the catalysts described herein is characterized as peptized until the desired dispersibility or a "dispersible alumina," as defined above, is achieved. According to one or more specific embodiments, the use of a highly dispersible alumina allows more of the surface area of the Cu to be exposed for reaction and thus may provide a higher catalytic activity. In one or more embodiments, the peptized alumina has a particle size of 1 μm or less. In one more embodiments, the alumina has 40% or greater dispersibility in water after peptizing at a pH of 2 to 5. That is, the percentage of alumina having a particle size of 1 μm or less in water after peptizing at a pH of 2 to 5 is at least 40%. In one more embodiments, the alumina has 50% or greater dispersibility in water after peptizing at a pH of 2 to 5. In a more specific embodiment, the alumina has 80% or greater dispersibility in water after peptizing at a pH of 2 to 5. Other suitable alumina may have 90% or greater dispersibility in water after peptizing at a pH of 2 to 5. In one or more alternative embodiments, non-dispersible alumina may be used in combination with dispersible alumina. In such embodiments, the non-dispersible alumina is milled into a fine powder before use.

The catalyst may, in certain embodiments, include alumina which may be formed or derived from boehmite, pseudoboehmite and combinations thereof. Suitable boehmite and pseudoboehmites have 70% or greater dispersibility in water after peptizing at a pH of 2 to 5. For example, suitable aluminas are available from Sasol North America Inc. of Houston, Tex., under the trademarks Catapal®, Pural®, Dispersal®, and Dispal®. Examples of aluminas that may be utilized in the catalysts described herein include aluminas available under the trade names Catapal® A, B, Cl, and D and Pural SB. A specific example of a suitable alumina is available under the trade name CATAPAL® D and has a particle size $d_{50}$ of about 40 μm. The alumina available under the trade name CATAPAL® D also has a BET surface area of 220 $m^2/g$ and a pore volume of about 0.55 ml/g after activation at 550° C. for 3 hours.

Accordingly, in certain specific embodiments, the alumina comprises dispersible alumina selected from one or more of boehmite, pseudoboehmite, and mixtures thereof. In alternative embodiments wherein the catalyst composite comprises dispersible alumina, at least a portion of the dispersible alumina is replaced with a nondispersible alumina. In a specific embodiment, at least a portion of the dispersible alumina is replaced with a γ-alumina. In another specific embodiment wherein the catalyst composition comprises boron oxide, the alumina comprises gamma alumina.

In other embodiments, at least a portion of the alumina comprises alumina prepared by peptizing dispersible alumina with a dispersibility of at least about 50% or greater and reacting the alumina with precursors of CuO, ZnO, and $ZrO_2$. In a specific embodiment, a portion of the alumina comprises alumina prepared by peptizing dispersible alumina with a dispersibility of at least about 50% or greater.

As will be understood, other sources of alumina can be used and include such diverse materials as aluminum nitrate. Some dispersible alumina sources are thought to be unsuitable for industrial scale applications because of their tendency to gel or become solid under normal operating conditions in an industrial or large-scale setting. Accordingly, many known catalysts and methods of making and using such catalysts utilized aluminum nitrate as an alumina source. Specifically, as stated above, the Cu of one or more catalysts described herein is highly dispersed by the reaction of an alumina derived by peptizing of boehmite or pseudoboehmite and precursors of ZnO, CuO, $ZrO_2$ and/or $CeO_2$.

Preparation

A second aspect of the present invention pertains to a method of preparing a catalyst composition as described herein. In one or more embodiments, the catalyst composition is formed by preparing two powders, followed by mixing and/or pelleting the two powders. In one or more embodiments, the first powder is a methanol-active component, and the second powder is an acidic component. In one or more embodiments, the first powder will make up about 70 to about 90% by weight of the total catalyst, and the second powder will constitute about 10 to 30% by weight of the total catalyst composite, and about 0-10% by weight of the catalyst composite may comprise an additive.

In one or more embodiments, the first powder includes ZnO, $ZrO_2$ and CuO, and in some embodiments $CeO_2$, which are formed from various precursors. For example salts of copper, zinc or aluminum are dissolved in a solvent, in particular water. At least two salts of either copper, zinc, or aluminum can be dissolved in a solvent, heated and a basic solution can be prepared and added. Both solutions can be added in parallel to the template, until the salt-solution is consumed. After this the suspension is filtered, dried, and calcined under air or inert gas flow. Non-limiting examples of anions in the salts for copper, zinc, or aluminum are selected from the group consisting of, nitrate, acetate, carbonate, halide, nitrite, sulfate, sulfite, sulfide, phosphate ion or silicate. Specifically, salts of copper, zinc or aluminum formed with the above mentioned anions can be converted into oxides of copper, zinc or aluminum applying a calcination step.

A suitable $ZrO_2$ precursor includes zirconyl nitrate, though other known precursors may be utilized. When zirconyl nitrate is used as the zirconia precursor, the $ZrO_2$ precursor is provided by forming a slurry of zirconyl nitrate and water. In such embodiments, it is desirable to maintain the reaction mixture or the zirconyl nitrate and water slurry at a pH of less than about 2, and in specific embodiments at a pH of less than about 1.5 or 1. In one or more specific embodiments, the reaction mixture or the zirconyl nitrate slurry is maintained at a pH of about 1. In one or more embodiments, the reaction mixture is maintained or has a temperature in the range from about 20° C. to about 30° C. In one or more embodiments, the temperature of the zirconyl nitrate slurry may be maintained at a temperature of about 25° C.

A suitable CuO precursor includes copper nitrate. A suitable ZnO precursor includes zinc nitrate. In one or more embodiments, the catalyst is formed by first reacting a $ZrO_2$ precursor with the peptized alumina to provide a first reaction product, a mixed slurry or a new slurry. A second reaction is then performed in which the CuO and ZnO precursors are reacted in a separate vessel to form or provide a second reaction product. The first reaction product and second reaction product are then subsequently mixed together.

In certain embodiments, the method includes peptizing a highly dispersible alumina to form a peptized alumina and reacting the peptized alumina with precursors of ZnO, $ZrO_2$ and CuO, and in some embodiments $CeO_2$, as described above. A highly dispersible alumina, as otherwise described herein, is prepared by adding the alumina to water to provide approximately 5 wt % to 35 wt % solids. The alumina and water mixture is mixed at high shear for approximately one hour to form a slurry. In one or more embodiments, the alumina and water mixture is maintained at a pH in the range from about 2 to about 5 during the mixing process at a temperature in the range from about 20° C. to about 30° C. In a specific embodiment, the alumina and water is maintained at a pH of about 3 during the mixing process. In an even more specific embodiment, the temperature of the alumina and water is maintained at about 25° C. The pH of the alumina and water mixture is maintained by adding an amount of acid to the mixture. Examples of suitable acids include nitric acid, formic acid, other known acids and combinations thereof. As described herein, in one or more embodiments the dispersible alumina may be replaced with nondispersible alumina. For example, up to 99% of the dispersible alumina may be replaced with nondispersible alumina that may include γ-alumina, η-alumina, χ-alumina, other transitional aluminas, boehmite, pseudoboehmite, gibbsite, bayerite, and mixtures thereof. In one or more embodiments, the alumina consists essentially of γ-alumina. In other embodiments, the alumina consists essentially of dispersible alumina. In yet other embodiments, the alumina comprises both γ-alumina and dispersible alumina. In further embodiments, the ratio of γ-alumina to dispersible alumina ranges from about 10:90 to 90:10, 20:80 to 80:20, 30:70 to 70:30, 40:60 to 60:40 or 50:50. In one or more embodiments, the ratio of γ-alumina to dispersible alumina is about 10:90, 20:80, 30:70, 40:60, 50:50, 60:40, 70:30, 80:20, or 90:10.

A first reaction product containing the $ZrO_2$ precursor may be prepared as a slurry in a separate vessel from the highly dispersible alumina. The process includes maintaining the $ZrO_2$ precursor at a low pH and a controlled temperature. In one or more embodiments, the $ZrO_2$ precursor is maintained at a pH of less than 2 or less than about 1.5. In one or more specific embodiments, the $ZrO_2$ precursor is maintained at a pH in the range from about 1.0 to about 2.0. In a more specific embodiment, the $ZrO_2$ precursor is maintained at a pH of about 1.0. The temperature of the $ZrO_2$ precursor of one or more embodiments is maintained at a temperature in the range from about 20° C. to about 30 ° C. In one or more specific embodiments, the $ZrO_2$ precursor is maintained at a temperature in the range from about 22° C. to about 28° C., or, more specifically, in the range from about 24° C. to about 26° C. In one variant, the $ZrO_2$ precursor is maintained at a temperature of about 25° C. In one or more embodiments, a cerium oxide precursor is added to the zirconium oxide precursor during the preparation of the first reaction product.

In one or more embodiments, the CuO and ZnO precursors are prepared separately for reaction with the first reaction product, new slurry or mixed slurry. In a separate vessel, a solution of the CuO precursor and ZnO precursor is prepared to form a second reaction product. In one or more specific embodiments, the second reaction product is provided by forming a solution of copper nitrate and zinc nitrate in a separate vessel. The temperature of second reaction product is maintained at a temperature in the range from about 30° C. to about 50° C. In one or more specific embodiments the temperature of the second reaction product is maintained at about 40° C. In one variant, the pH of the second reaction product is maintained at a pH of less than about 1.5 or, in a more specific variant, at about 1. In one or more specific embodiments, the second reaction product is maintained at this pH by the addition of soda ash, or other suitable sodium source, for example, sodium hydroxide, sodium carbonate or sodium bicarbonate.

The second reaction product is then added to the first reaction product or mixed slurry to create a third reaction product. The first reaction product and the second reaction product are well mixed for a duration from about 30 minutes to about 60 minutes. The temperature and/or pH may be adjusted or controlled to create an acidic slurry. The acidic slurry may contain copper nitrate, zinc nitrate, zirconyl nitrate, and cerium nitrate.

In one or more embodiments, the third reaction product is maintained at a pH of less than about 1.5, or in a more specific embodiment, at about 1 or as close to about 1 as possible. The temperature may also be controlled. For example, in one variant, the temperature of the third reaction product is raised and maintained at a temperature in the range from about 30° C. to about 50° C. In one or more specific embodiments, the temperature of the third reaction product is raised and maintained at a temperature of about 40° C.

The dispersed alumina and water slurry is added to and is well mixed for a duration from about 30 minutes to about 60 minutes to form a fourth reaction product, new slurry or mixed slurry. While the alumina slurry and the third reaction product are mixed, the pH is maintained at less than about 1.5. In one or more embodiments, the process includes maintaining the pH at about 1 or as close to 1 as possible. The temperature is also maintained at a range from about 20° C. and about 30° C. or, more specifically, at 25° C.

The fourth reaction product is then combined with a precipitation solution and a heel of water to form a precipitate slurry. The precipitation solution may include a basic solution of one or more of sodium carbonate and sodium bicarbonate and is formed separately from the heel of water. The precipitation solution may be formed at a temperature and/or have a temperature in the range from about 30° C. to about 70° C. or, in one or more specific embodiments, a temperature of about 40° C. In one or more embodiments, the slurry is formed by adding the acidic slurry and the precipitate solution simultaneously and slowly to a separate vessel containing a heel of water to form a precipitate slurry. The heel of water may have a temperature in the range from about 30° C. to about 70° C. or, in one or more specific embodiments, a temperature of about 40° C. This simultaneous addition of the acidic slurry and the precipitation solution improves the consistency in the precipitation of the carbonates.

In one or more embodiments, precipitation reaction is performed or carried out at a pH that is controlled, for example, by adjusting the flow of the fourth reaction product and/or the flow of the precipitation solution. In one or more embodiments, the pH is controlled to an amount in the range from about 6 to about 7 or, more specifically, in the range from about 6.4 to about 6.7. In one or more specific embodiments, the pH is controlled at about 6.5. The temperature of the precipitation may be carried out at a temperature in the range from about 30° C. to about 70° C., or more specifically, a temperature of about 40° C.

In one or more embodiments, the precipitate slurry is digested or aged for a duration of about 15 minutes to about 15 hours. In a specific embodiment, the precipitate slurry is digested or aged for a duration of about 1 hour to about 3 hours. In an even more specific embodiment, the precipitate slurry is digested or aged for a duration of about 2 hours. The temperature of the precipitate slurry is increased to a temperature in the range from about 30° C. to about 70° C. during aging or, more specifically, to a temperature of about 60° C. In one variant, the pH of the precipitate slurry during digestion or aging is not controlled. In such embodiments, the pH of the precipitate slurry undergoes some changes by increasing and decreasing, though the amount of increase and decrease may not be uniform. During the digestion or aging process, the color of the slurry changes from blue to green. In one variant, the method includes filtering and washing the slurry to form a filter cake. The method may also include drying the filter cake to form a dry filter cake or dried powder. The dry filter cake or dried powder may then be calcined to decompose any carbonates to oxides. In one or more embodiments, the dry filter cake or dried powder may be calcined for a duration of about 2 hours at a temperature range of about 300° C. to about 500° C. to form the first powder. In one or more embodiments, the dry filter cake or dried powder may be calcined for a duration of about 2 hours at a temperature of about 350° C. to form the first powder.

In a specific embodiment of the method, at least a part of the first powder is prepared by a precipitation reaction and/or calcination. In one or more embodiments, precursors of the first powder comprise a salt in a solution and can be heated and adjusted to a defined pH-value. After this, a calcination step may be carried out. In another specific embodiment of the method, at least one component of the first powder is precipitated and at least one part of the first powder, (which is not subjected to the first precipitation) is added to the precipitate. In an even more specific embodiment, it is added by spray drying or precipitation.

In certain embodiments, the first powder has a particle size distribution characterized by a $D_{10}$ value of 5-140 μm, a $D_{50}$ value of 40-300 μm, and a $D_{90}$ value of 180-800 μm. This particle size distribution can be determined via state of the art analysis techniques, e.g. via analysis apparatus like Mastersizer® 2000 or 3000 by Malvern Instruments GmbH. The particle size distribution in the sense of the invention is characterized by the $D_{10}$, $D_{50}$, and $D_{90}$ value. As used herein, "$D_{10}$" refers to the equivalent diameter where 10 mass % of the particles of the sample has a smaller diameter and hence the remaining 90% is coarser. The definition of $D_{50}$ and $D_{90}$ can be derived similarly. In specific embodiments, the first powder has a particle size distribution characterized by a $D_{10}$ value of 5-80 μm, a $D_{50}$ value of 40-270 μm, and a $D_{90}$ value of 250-800 μm. In particular embodiments, the first powder has a particle size distribution characterized by a $D_{10}$ value of 5-50 μm, a $D_{50}$ value of 40-220 μm, and a $D_{90}$ value of 350-800 μm.

The final composition of the first powder may be varied. In one or more embodiments, the amount of copper oxide ranges from about 50% to about 55% weight of the total weight of the first powder. In some embodiments, the amount of zinc ranges from about 16% to about 20% of the total weight of the first powder. In one or more embodiments, the amount of zirconium ranges from about 14% to about 15% by weight of the total weight of the first powder. In some embodiments, the amount of cerium ranges from about 14% to about 15% by weight of the total weight of the first powder. In one or more embodiments, the amount of alumina ranges from about 20% to about 30% by weight of the total weight of the first powder.

In one or more embodiments, the second powder comprises one or more of aluminum hydroxide, aluminum oxide hydroxide and/or γ-aluminum oxide with one or more of niobium, tantalum, phosphorus or boron, or mixtures thereof. The second powder may be generally made by the calcination of a salt comprising niobium, tantalum, phosphorus or boron with a mixture of aluminum hydroxide, aluminum oxide hydroxide and/or γ-aluminum oxide. In one embodiment, the salt further comprises one or more of oxalate, acetate and acetylacetonate. In some embodiments, the second powder comprises at least some γ-alumina, which can provide acid sites. In such embodiments, the resulting catalyst composition will contain at least some γ-alumina even if the first powder does not contain γ-alumina. In one or more embodiments, the amount of alumina ranges from about 80 to about 90% by weight of the total weight of the second powder.

In some embodiments, the niobium, tantalum, phosphorus and/or boron oxide are present in amount as low as about 0.1 or 1 percent by weight, and as high as about 20, 30 or 40 percent by weight of the catalytic material. In a specific embodiment, the second powder comprises one or more of aluminum hydroxide, aluminum oxide hydroxide and γ-aluminum oxide with about 1-25, 5-20, 10-15 or 1-10% by weight of one or more of niobium, with about 1-25, 5-20, 10-15 or 1-10% by weight of tantalum, with about 1-25, 5-20, 10-15 or 1-10% by weight of phosphorus or with about 1-25, 5-20, 10-15 or 1-10% by weight of boron.

In one or more embodiments of the catalyst composition, the resulting material from the second powder has a surface area from about 40, 50, 60, 70, 100 or 130 to about 170, 200, 240, 250 or 270 m$^2$/g, with a pore volume in the range of from about 0.35-0.1.45 ml/g, and specifically a surface area from about 55, 85, 100 or 125 to about 140, 160, 180 200 or 220 m$^2$/g with a pore volume in the range of from about 0.35-1.35 ml/g, and even more specifically a surface area from about 110-200 m$^2$/g with a pore volume in the range of from about 0.51-1.14 ml/g.

In a specific embodiment of the catalyst composition, the resulting material from the second powder comprises boehmite, and more specifically a boehmite-containing mineral. Boehmite occurs in tropical laterites and bauxites developed on alumino-silicate bedrock. It also occurs as a hydrothermal alteration product of corundum and nepheline. It occurs with kaolinite, gibbsite and diaspore in bauxite deposits and with nepheline, gibbsite, diaspore, natrolite and analcime in nepheline pegmatites.

The second powder that is used can vary as described above. In certain embodiments, the second powder has a size distribution characterized by a $D_{10}$ value of 5-140 μm, a $D_{50}$ value of 40-300 μm, and a $D_{90}$ value of 180-800 μm. The particle sizes of the two powders may be the same or different. In preferred embodiments, the second powder has a particle size distribution characterized by a $D_{10}$ value of 5-80 μm, a $D_{50}$ value of 40-270 μm, and a $D_{-90}$ value of 250-800 μm. In particular embodiments, the second powder has a particle size distribution characterized by a $D_{10}$ value of 5-50 μm, a $D_{50}$ value of 40-220 μm, and a $D_{90}$ value of 350-800 μm.

Additives

In one or more embodiments, additives may be included in the catalyst composition. For example, an additive can be a structure-promoter, which can help to build up pores or channels. Examples of a structure-promoter include, but are not limited to, thermally decomposable compounds like polymers, wood dust, flour, graphite, film material, straw, stearic acid, palmitic acid, celluloses or combinations thereof.

Mixing and/or Pelleting of the Two Powders

In one or more embodiments, the two dried powders are mixed together, meaning that they are brought into contact without further chemical modification. In one variant, the catalyst composition comprises about 70-90% by weight of the first powder, about 10-90% by weight of the second powder, and about 0-10% by weight of one or more additives (these three components total 100%).

In several embodiments, the catalyst composition can be in any form known in the art that contains pores or channels or other features for enlargement of surface, which will help to bring the educts in contact such that they can react with the syngas to form the desired product. In one or more embodiments, the catalyst composition can be understood as a physical mixture, whereby the powders contact each other and exhibit channels and/or pores between their contact surfaces. In a specific embodiment, the powders are not melted or sintered at their contact surfaces.

In one or more embodiments, the catalyst composition is a pellet with a size in the range from 1×1 mm to 10×10 mm, specifically in the range from 2×2 mm to 7×7 mm. The pellet is obtained by pressing the mixture of the two powders (along with any other promoters or components) into a pellet. In various embodiments, the pellet can be ring-shaped, star-shaped or spherical-shaped, hollow strings, trilobes, multi-hole pellets, extrudates and alike.

In particular, the powders and any other components can be compacted in a presser, a squeezer, a crusher or a squeezing machine. In one or more embodiments, compacting means that particles of a defined particle size distribution are pressed together, which have a diameter in the range of 1 to 10 mm and a height of 1 to 10 mm. In specific embodiments, the particle size distribution is left intact after the compaction.

In a specific embodiment of the method, a pellet is formed with a size in the range of from about 1×1 mm to 10×10 mm, and specifically in the range from 2×2 mm to 7×7 mm.

In one embodiment of the method, the two powders are independently pressed through at least one sieve, wherein the sieve exhibits a mesh size from about 0.005 to about 5 mm in order to obtain a particle size distribution characterized by a $D_{10}$ value of about 5-140 μm, a $D_{50}$ value of about 40-300 μm, and a $D_{90}$ value of about 180-800 μm. Specifically, the sieve exhibits a mesh size from about 0.005 to about 1.5 mm, and even more specifically a mesh size from about 0.005 to about 0.9 mm. In another embodiment, the particles can also exhibit particle size distribution characterized by a $D_{10}$, $D_{50}$, and $D_{90}$ value of about 5-140 μm, about 40-300 μm, and about 180-800 μm, respectively.

In a specific embodiment of the preparation of a catalyst composition described herein, at least three different sieves are used, wherein the two powders are pressed through the sieves starting from the sieve with the largest mesh size and progressing in mesh size order to the sieve with the smallest mesh size. Specifically, in one or more variants, the particle size distribution of the first and/or second powder may be characterized by a $D_{10}$ value of about 5-140 μm, a $D_{50}$ value of about 40-300 μm, and a $D_{90}$ value of about 180-800 μm. These particles can also be broken during the sieving, so that smaller particles are obtained that can be passed on through to the smaller sized sieve. Therefore, a first fraction with a particle size distribution can be obtained before the second sieve. This fraction can also be used as a catalyst composition. Additionally, in embodiments with three sieves, the particles which go through the second sieve with a mesh size smaller than the first sieve, but bigger than the third sieve, can be obtained behind the second sieve and before the smallest sieve with the smallest mesh size. Again, the particles obtained after the second (middle) sieve can be used as a catalyst composition. In addition to this, the particles obtained after the sieve with the biggest mesh size could be pressed through the second sieve in order to reduce the particle size.

In a specific embodiment, the preparation method further comprises adding a mixture of hydrogen and nitrogen. The mixture of hydrogen and nitrogen may be added to the first and/or second powder. In a very specific embodiment, content of the volume of the hydrogen is less than 5% of the mixture.

In one or more embodiments, the resulting catalyst, containing both powders and before reduction of the copper oxide to form copper metal, includes cupric oxide in an amount in the range from about 10% by weight to about 75%, or about 15% to about 50% by weight of the total catalyst. It is noted that the amounts of the various components will depend on the ratio of the two powders utilized. In one variant, ZnO is present in the resulting catalyst, before reduction, in an amount in the range from about 5% by weight to about 70%, about 5% to about 50%, or about 5% to about 25% by weight. In one or more embodiments, the catalyst includes $ZrO_2$ in an amount in the range from about 1% by weight to about 50%, or about 1% to about 25% by weight, before reduction. In one or more embodiments, the catalyst includes cerium oxide in an amount in the range of from about 5% by weight to about 70%, about 5% to about 50%, or about 5% to about 25%, before reduction. In one or more embodiments, the catalyst includes niobium oxide, tantalum oxide, phosphorus oxide and/or boron oxide in an amount in the range from about 1% by weight to about 50%, or about 1% to about 40% by weight, before reduction. In one or more embodiments, the catalyst includes alumina in an amount in the range from about 5% by weight to about 80%, or about 10% to about 60% by weight, before reduction. This alumina amount is the total alumina from both powders.

In one or embodiments, the prepared catalyst composition is further reduced. A variant of the reducing step utilizes a hydrogen-containing gas. Specifically, such methods may include heating the catalyst to a temperature in the range from about 150° C. to about 200° C. while flowing nitrogen gas at atmospheric pressure over the catalyst in a reactor. In one or more specific embodiments, the catalyst is heated to a temperature in the range from about 165° C. to about 185° C. in flowing $N_2$. In a more specific embodiment, the catalyst is heated to a temperature of about 170° C. in flowing $N_2$. The nitrogen is replaced incrementally by hydrogen. In one or more embodiments, the temperature may be slowly and incrementally increased to a maximum of about 250° C.

The resulting catalyst composition includes copper metal, formed form the reduction of the CuO precursor. The catalyst also includes ZnO, $ZrO_2$, niobium oxide which function as promoters or active materials, while the alumina functions as a structural component. In some embodiments, the catalyst composition also comprises ceria. In one or more embodiments, at least the ZnO, $ZrO_2$, and/or cerium oxide are closely associated with the copper metal.

DME Synthesis

In one or more embodiments, the catalyst composition exhibits the ability to directly convert synthesis gas to dimethyl ether. The catalyst compositions described herein are able to convert carbon monoxide at levels close to the thermodynamic limits, as compared to commercially available catalyst compositions at similar testing conditions (e.g., 84% conversion versus about 55% conversion at 250° C., 50 bar, GHSV=2400 $h^{-1}$, $H_2/CO=1$). This is highly advantageous, as normally two steps are required in the synthesis of dimethyl ether: conversion of synthesis gas to methanol, and then conversion of methanol to the dimethyl ether end product.

Thus, another aspect of the present invention pertains to a method of making dimethyl ether. The method comprises contacting a stream of synthesis gas comprising carbon monoxide and hydrogen with a catalyst comprising about 10 to about 75 weight % CuO; about 5 to about 50 weight % ZnO; about 1 to about 30 weight % $ZrO_2$; about 1 to about 40 weight % of one or more of boron oxide, tantalum oxide, niobium oxide, phosphorus oxide and combinations thereof; and-about 5 to about 80 weight % alumina. In one embodiment, the synthesis gas has a ratio of carbon monoxide to hydrogen is about 1. In an alternate variant, the synthesis gas has a ratio of carbon monoxide to hydrogen is less than 1. In yet another variant, the synthesis gas has a ratio of carbon monoxide to hydrogen is greater than 1. In one or more embodiments, the synthesis gas further comprises carbon dioxide. Thus, in yet another embodiment, the catalyst composition is contacted with a synthesis gas comprising carbon dioxide.

In other embodiments, the method of making DME further comprises reducing the catalyst composition, wherein the stream of synthesis gas is contacted with the reduced catalyst composition. In variants of this embodiment, the catalyst composition is reduced at a temperature having a range of about 140° C. to about 240° C., and may have one or more of nitrogen, hydrogen, and a mixture thereof. In some embodiments, a reactor may be filled with the catalyst composition. In some specific embodiments, a reactor is filled with pelletized version of the catalyst composition.

One or more of the embodiments of this method relates to a high turnover of carbon monoxide. The reaction conditions are selected to achieve suitable DME synthesis. In some embodiments, the temperature is about 180° C. to 300° C., or 200° C. to 300° C., or 200° C. to 250° C. Suitable pressures for the synthesis of DME include, but are not limited to, about 20 to 80 bar, and in particular from 30 to 50 bar.

Without intending to limit the invention in any manner, embodiments of the present invention will be more fully described by the following examples.

EXAMPLES

Example 1

Syntheses of Three Different Methanol-active Components

Synthesis of A

Two solutions are prepared for the precipitation of the components:

Solution 1: A solution of 1.92 kg copper nitrate, 0.58 kg zinc nitrate, 0.51 kg zirconia nitrate and 0.66 kg pseudoboehmite alumina dispersion are dissolved/mixed in 2.84 L water.

Solution 2: 1.147 kg sodium carbonate is dissolved in 3.841 L water.

Both solutions are separately heated to 40° C. A mix pot containing 2.13 L water is heated to 40° C. Solution 1 and Solution 2 are simultaneously added to the mix pot with agitation while maintaining a pH=6.5+/−0.20 for 90 minutes. The precipitation ends once Solution 1 is consumed. The temperature is raised to 60° C. for 2 hours while maintaining agitation. The precipitate is filtered and washed with 60° C. deionized water until sodium oxide content is <0.10% and free of nitrates. The filter cake is dried at 120° C. overnight and calcined for 4 hours at 350° C. in air. The metal oxide content of the catalyst in wt. % is as follows CuO 48.0: ZnO 17.0: $Al_2O_3$ 23.0: $ZrO_2$ 12.0.

Synthesis of B

Two solutions are prepared for the precipitation of the components:

Solution 1: A solution of 1.92 kg copper nitrate, 0.58 kg zinc nitrate, 0.51 kg zirconia nitrate and 0.66 kg Catapal® D alumina are dissolved/mixed in 2.84 L water.

Solution 2: 1.147 kg sodium carbonate is dissolved in 3.841 L water

Both solutions are separately heated to 40° C. A mix pot containing 2.13 L water is heated to 40° C. Solution 1 and Solution 2 are simultaneously added to the mix pot with agitation while maintaining a pH=6.5+/−0.20 for 90 minutes. The precipitation ends once Solution 1 is consumed. The temperature is raised to 60° C. for 2 hours while maintaining agitation. The precipitate is filtered and washed with 60° C. deionized water until sodium oxide content is <0.10% and free of nitrates. The filter cake is dried at 120° C. overnight and calcined for 4 hours at 350° C. in air. The metal oxide content of the catalyst in wt.% is as follows CuO 50.7: ZnO 15.4: $Al_2O_3$ 20.2: $ZrO_2$ 13.7.

Synthesis of C

Two solutions are prepared for the precipitation of the components:

Solution 1: A solution of 1.75 kg copper nitrate, 0.55 kg zinc nitrate, 0.46 kg zirconia nitrate, 0.74 kg gamma alumina suspension and 73.7 g cerium nitrate are dissolved/mixed in 2.84 L water.

Solution 2: 1.147 kg sodium carbonate is dissolved in 3.841 L water.

Both solutions are separately heated to 40° C. A mix pot containing 2.13 L water is heated to 40° C. Solution 1 and Solution 2 are simultaneously added to the mix pot with agitation while maintaining a pH=6.5+/−0.20 for 90 minutes. The precipitation ends when Solution 1 is consumed. The temperature is raised to 60° C. for 2 hours while maintaining agitation. The precipitate is filtered and washed with 60° C. deionized water until sodium oxide content is <0.10% and free of nitrates. The filter cake is dried at 120° C. overnight and is calcined for 4 hours at 350° C. in air. The metal oxide content of the catalyst in wt.% is as follows CuO 50.5: ZnO 16.5: $Al_2O_3$ 20.5: $ZrO_2$ 9.5: $CeO_2$ 3.0.

Example 2

Syntheses of the Acidic Components

Synthesis of X

A solution is prepared that consists of 4 grams ammonium niobate(V) oxalate and 27.4 ml demineralized water. This solution is applied onto a 40 g $Al_2O_3$/AlOOH-mixture (crushed extrudates consisting of 60% gamma- $Al_2O_3$ and 40% boehmite) by spray-watering. This material is then dried for 12 h at 90° C. in a drying oven. After drying, the material is calcined in a rotating tube for 3 hours at 450° C. under a nitrogen atmosphere (30 nl/h). The heating rate is 5° C./min. After cooling to room temperature, the material is ready for use.

Synthesis of Y

A solution is prepared that consists of 4 grams boronic acid and 27.4 ml demineralized water. This solution is applied onto a 40 g $Al_2O_3$/AlOOH-mixture (crushed extrudates consisting of 60% gamma- $Al_2O_3$ and 40% boehmite) by spray-watering. This material is then dried for 12 h at 90° C. in a drying oven. After drying, the material is calcined in a rotating tube for 3 hours at 450° C. under a nitrogen atmosphere (30 nl/h). The heating rate is 5° C./min. After cooling to room temperature, the material is ready for use.

Synthesis of Z

An solution is prepared that consists of 4 grams phosphoric acid and 27.4 ml demineralized water. This solution is applied onto a 40 g $Al_2O_3$/AlOOH-mixture (crushed extrudates consisting of 60% gamma- $Al_2O_3$ and 40% boehmite) by spray-watering. This material is then dried for 12 h at 90° C. in a drying oven. After drying, the material is calcined in a rotating tube for 3 hours at 450° C. under a nitrogen atmosphere (30 nl/h). The heating rate is 5° C./min. After cooling to room temperature, the material is ready for use.

Example 3

Preparation of the Final Catalyst Composition

The methanol-active compound and the acid compound are compacted separately in a tablet press and/or pelletizing machine. The molding obtained (diameter=ca, 25 mm, height=ca, 2 mm) is squeezed through sieves with an appropriate mesh size, so that the desired split fraction is obtained. From both fractions the proper quantity is weight in (9/1, 8/2, or 7/3 methanol-active/acidic compound) and mixed in a mixing machine (Heidolph Reax 2 or Reax 20/12). Any promoters or additional components are added in advance of pelletization.

Example 4

Testing Conditions for Non-Pelletized Mixtures

The catalyst composition (5 cm³ by volume) is incorporated into a tubular reactor (inner diameter 0.4 cm, bedded in a metal heating body) on a catalyst bed support consisting of alumina powder as a layer of inert material, and is then pressure-less reduced with a mixture of 1 Vol.-% $H_2$ and 99 Vol.-% $N_2$. The temperature is increased in intervals of 8 hours from 150° C. to 170° C., 170° C. to 190° C. and finally to 230° C. At a temperature of 230° C. the synthesis gas is introduced and heated within 2 hours up to 250° C. The synthesis gas consists of 45% $H_2$ and 45% CO and 10% inert gas (argon). The catalyst composition is run at an input temperature of 250° C., GHSV of 2400h$^{-1}$ and a pressure of 50 bar.

Example 5

Testing Conditions for Pelletized Mixtures

Tests for pelletized materials are conducted in a similar test rick compared to the setup described above for non-pelletized materials using the same routine. The only difference is that the tubular reactor does not have an inner diameter of 0.4 cm, but instead an inner diameter of 3 cm. The tests for the pelletized materials are carried out with a catalyst volume of 100 cm³.

Example 6

Results

Table 1 shows the results of various catalyst compositions. In comparison to the state of the art (see also PhD thesis "Dimethylether-Direktsynthese aus kohlenmonoxidreichem Synthesegas"—Miriam Stiefel, University of Heidelberg, 03. December 2010) the catalyst performances shown in table 1. Experiments 1-5 reveal that significant higher CO conversions are achieved. Furthermore the catalysts show very low S(Others) values.

Inventive experiment 6 was done using 3×3 mm pellets that were formed of a physical mixture of A and Z that were mixed in a ratio by weight of 4/1. It can be seen that the superior performance is maintained within this catalyst composition compared to Experiment 5.

TABLE 1

Results

| Exp. No. | MeOH-active component A, B, or C | acidic component X, Y, or Z | CO conversion [%] | S(MeOH) | S(DME) | S(CO2) | S(Others) |
|---|---|---|---|---|---|---|---|
| 1 | A | X | 76.22 | 11.13 | 48.31 | 40.4 | 0.16 |
| 2 | B | X | 63.17 | 13.18 | 47.68 | 39.06 | 0.08 |
| 3 | C | X | 76.39 | 6.43 | 48.95 | 44.35 | 0.27 |
| 4 | A | Y | 78.63 | 5.18 | 45.94 | 48.69 | 0.19 |
| 5 | A | Z | 81.72 | 2.43 | 47.50 | 49.98 | 0.09 |
| 6 | 3 × 3 mm pellet of A & Z | | 79.54 | 1.94 | 48.97 | 49.07 | 0.02 |

All mixtures comprise MeOH-active and acidic components in a weight ratio of 4/1.
All gaseous streams were analyzed via online-GC. Argon was used as internal standard to correlate in and off gas streams.
CO conversion is given as follows: $(CO_{in} - (CO_{out} * Argon_{in}/Argon_{out}))/CO_{in} * 100\%$
S(MeOH) = Volume (MeOH) in product stream/Volume (MeOH + DME + $CO_2$ + Others without hydrogen and CO) in product stream * 100%
S(DME) = Volume (DME) in product stream/Volume (MeOH + DME + $CO_2$ + Others without hydrogen and CO) in product stream * 100%
S($CO_2$) = Volume ($CO_2$) in product stream/Volume (MeOH + DME + $CO_2$ + Others without hydrogen and CO) in product stream * 100%
S(Others) = Volume (Others) in product stream/Volume (MeOH + DME + $CO_2$ + Others without hydrogen and CO) in product stream * 100%
"Others" are compounds that are formed out of $H_2$ and CO that are not MeOH, DME, or $CO_2$.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A catalyst composition for the synthesis of dimethyl ether comprising:
    about 10 to about 75 weight % CuO;
    about 5 to about 30 weight % ZnO;
    about 1 to about 30 weight % $ZrO_2$;
    about 1 to about 40 weight % of one or more of boron oxide, niobium oxide, tantalum oxide, phosphorus oxide, and combinations thereof; and
    about 5 to about 80 weight % alumina, wherein at least a portion of alumina comprises γ-alumina and dispersible alumina having a dispersibility of at least about 40% or greater.

2. The catalyst composition of claim 1, wherein the catalyst composition further comprises ceria.

3. The catalyst composition of claim 2, wherein the catalyst composition comprises about 1 to about 30 weight % of ceria.

4. The catalyst composition of claim 1, wherein the catalyst comprises about 0.1 to about 20 weight % of one or more of boron oxide, tantalum oxide, phosphorus oxide, niobium oxide and combinations thereof.

5. The catalyst composition of claim 1, wherein the alumina further comprises one or more of η-alumina, χ-alumina, boehmite, pseudoboehmite, gibbsite, bayerite, and mixtures thereof.

6. The catalyst composition of claim 1, wherein the up to 99% of the dispersible alumina is replaced with η-alumina.

7. The catalyst composition of claim 5, wherein the up to 99% of the dispersible alumina is replaced with η-alumina.

8. The catalyst composition of claim 5, wherein the dispersible alumina has a dispersibility of at least about 70% or greater.

9. The catalyst composition of claim 1, wherein the ratio of η-alumina to dispersible alumina ranges from 10:90 to 90:10.

10. The catalyst composition of claim 1, wherein the catalyst composition comprises boron oxide, and the alumina comprises gamma alumina and dispersible alumina.

11. The catalyst composition of claim 1, wherein the catalyst composition comprises niobium oxide, and the alumina comprises gamma alumina and dispersible alumina.

12. The catalyst composition of claim 1, wherein at least a portion of the alumina comprises alumina prepared by peptizing dispersible alumina with a dispersibility of at least about 50% greater and reacting the alumina with precursors of CuO, ZnO, and $ZrO_2$.

13. The catalyst composition of claim 1, wherein a portion of the alumina comprises alumina prepared by peptizing dispersible alumina with a dispersibility of at least about 50% or greater.

14. The catalyst composition of claim 13, wherein the ratio of η-alumina to dispersible alumina ranges from about 10:90 to 90:10.

15. The catalyst composition of claim 13, wherein up to 99% of the dispersible alumina is replaced with η-alumina.

* * * * *